(12) United States Patent
Boccanfuso et al.

(10) Patent No.: US 9,081,876 B2
(45) Date of Patent: Jul. 14, 2015

(54) METHODS AND SYSTEMS FOR NAVIGATING IMAGE SERIES

(71) Applicants: Giovan Giuseppe Boccanfuso, Heidelberg (CA); Marc Alain Bernard, Elmira (CA)

(72) Inventors: Giovan Giuseppe Boccanfuso, Heidelberg (CA); Marc Alain Bernard, Elmira (CA)

(73) Assignee: AGFA HEALTHCARE INC., Toronto (CA)

( * ) Notice: Subject to any disclaimer, the term of this patent is extended or adjusted under 35 U.S.C. 154(b) by 83 days.

(21) Appl. No.: 13/948,502

(22) Filed: Jul. 23, 2013

(65) Prior Publication Data

US 2015/0030218 A1    Jan. 29, 2015

(51) Int. Cl.
*G06K 9/00* (2006.01)
*G06F 19/00* (2011.01)

(52) U.S. Cl.
CPC .................................... *G06F 19/321* (2013.01)

(58) Field of Classification Search
None
See application file for complete search history.

(56) References Cited

U.S. PATENT DOCUMENTS

| | | | |
|---|---|---|---|
| 7,812,826 B2 | 10/2010 | Ording et al. | |
| 7,822,254 B2 | 10/2010 | Yatziv et al. | |
| 8,320,647 B2 | 11/2012 | Djeridane | |
| 2010/0271398 A1 | 10/2010 | Apted | |
| 2011/0209057 A1 | 8/2011 | Hinckley et al. | |
| 2012/0176401 A1 | 7/2012 | Hayward et al. | |
| 2012/0194540 A1 | 8/2012 | Reicher et al. | |

OTHER PUBLICATIONS

Patel, Wiley "Apple awarded limited patent on pinch-to-zoom." Oct. 13, 2010, retrieved from <http://www.engadget.com> retrieved on Sep. 7, 2012.
Ladin, Miriametal. "Agfa HealthCare's IMPAX® 6 introduces volumetric management features at SIIM 2009", Jun. 2009, Retrieved online URL: http://www.agfahealthcare.com/global/en/main/news_events/news/archives; [retrieved on Feb. 20, 2013.].

*Primary Examiner* — Atiba O Fitzpatrick
(74) *Attorney, Agent, or Firm* — Bereskin & Parr LLP/S.E.N.C.R.L., s.r.l.

(57) ABSTRACT

A method and system are provided for navigating an image series that includes at least one image. The method and system involve receiving an input corresponding to a reference location; operating at least one processor for determining a target position in the image series based on the reference location, the at least one processor being configured to receive initial series data corresponding to an initial location in the image series and a separation distance corresponding to a distance between two sequential images in the image series; determine a target distance for the image series, the target distance corresponding to a distance from the reference location to the initial location; and determine the target position based on the separation distance and the target distance.

21 Claims, 10 Drawing Sheets

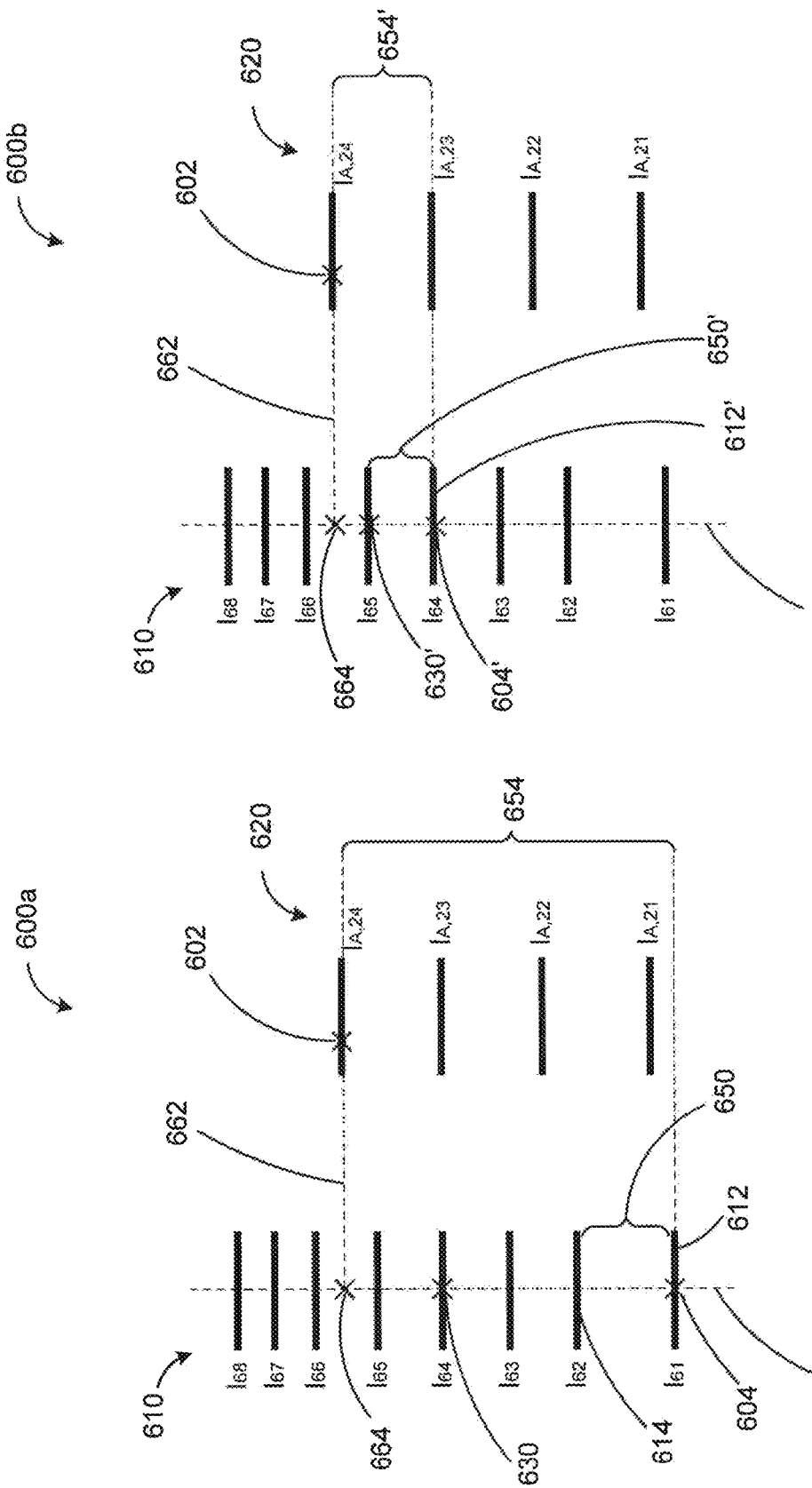

METHODS AND SYSTEMS FOR NAVIGATING IMAGE SERIES

FIELD

The described embodiments relate to methods and systems for navigating image series and in particular, for navigating image series based on a reference location.

BACKGROUND

When conducting a medical examination of a patient, medical professionals may review one or more series of medical images. The one or more series of medical images may be related. Often, it can be beneficial for the medical professional to review multiple related series of medical images simultaneously in order to assess the patient's condition and to recommend a course of treatment. The various related series of medical images can include images of the same anatomy at different times or at different planes, for example.

Navigation between the multiple related series of medical images, however, can be challenging. Manual navigation between different series of images by the medical professional can be time-consuming and unreliable.

Systems that enable automatic navigation as between different series of images can offer substantial advantages. However, existing systems require entire series of medical images to be stored on local memory for navigation. As a result, these systems can be memory intensive and exhibit slow performance. In particular, the slow performance may cause a substantial delay in the display of images, especially a first image in an image series.

SUMMARY

The various embodiments described herein generally relate to methods (and associated systems configured to implement the methods) for navigating an image series that includes at least one image. The method comprising receiving an input corresponding to a reference location; operating at least one processor for determining a target position in the image series based on the reference location, the at least one processor being configured to receive initial series data corresponding to an initial location in the image series and a separation distance corresponding to a distance between two sequential images in the image series; to determine a target distance for the image series, the target distance corresponding to a distance from the reference location to the initial location; and to determine the target position based on the separation distance and the target distance.

In accordance with an embodiment of the invention, there is provided a system for navigating an image series that includes at least one image. The system comprising at least one processor configured to receive an input corresponding to a reference location; receive initial series data corresponding to an initial location in the image series and a separation distance corresponding to a distance between two sequential images in the image series; determine a target distance for the image series, the target distance corresponding to a distance from the reference location to the initial location; and determine a target position in the image series based on the separation distance and the target distance.

In accordance with an embodiment of the invention, there is provided a non-transitory computer-readable medium comprising instructions executable on at least one processor for implementing a method for navigating an image series that includes at least one image. The method comprising receiving an input corresponding to a reference location; receiving initial series data corresponding to an initial location in the image series and a separation distance corresponding to a distance between two sequential images in the image series; determining a target distance for the image series, the target distance corresponding to a distance from the reference location to the initial location; and determining a target position in the image series based on the separation distance and the target distance.

BRIEF DESCRIPTION OF THE DRAWINGS

Several embodiments of the present invention will now be described in detail with reference to the drawings, in which:

FIGS. 6A to 6C illustrate verification of a target position in accordance with an example embodiment;

Figure 1:
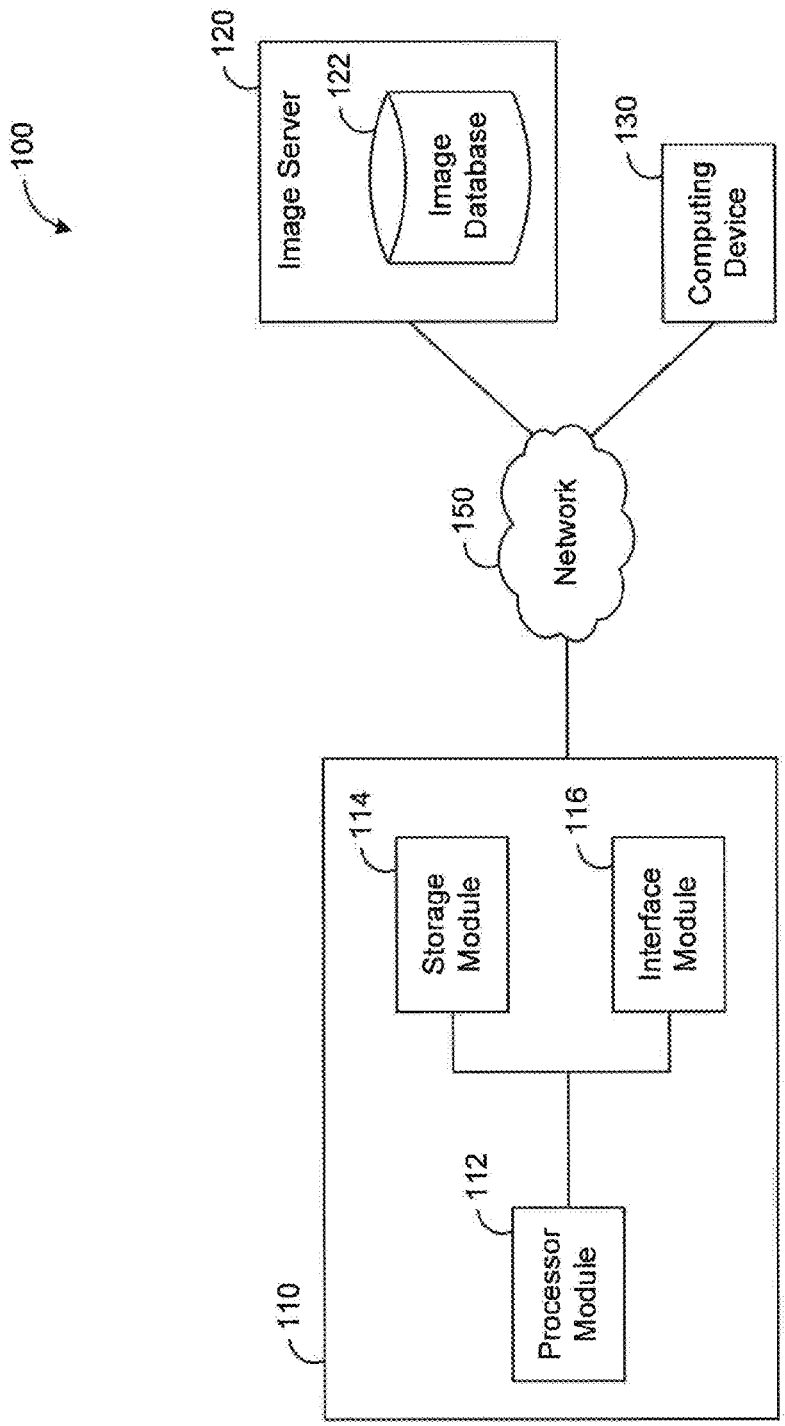
FIG. 1 is a block diagram of components interacting with an image navigation system in accordance with an example embodiment.

The drawings, described below, are provided for purposes of illustration, and not of limitation, of the aspects and features of various examples of embodiments described herein. The drawings are not intended to limit the scope of the description in any way. For simplicity and clarity of illustration, elements shown in the figures have not necessarily been drawn to scale. Where considered appropriate, for simplicity and clarity of illustration, reference numerals may be repeated among the figures to indicate corresponding or analogous elements or steps.

DESCRIPTION OF EXEMPLARY EMBODIMENTS

The various embodiments described herein generally relate to methods (and associated systems configured to implement the methods) for navigating one or more image series based on a reference location. The described methods may include receiving an input that corresponds to the reference location and determining a target position in at least one of the image series based on the reference location. The target position may correspond to a location or an image in the image series that is in closest spatial proximity to the reference location. For determining the target position, the navigation system may use information associated with the image series that is stored at the navigation system. The information may include initial series data that is associated with the image series. The initial series data may include data associated with an initial location in the image series and attributes of the image series, such as parameters for a normal to a first image of that image series. The information used by the navigation system may also include a separation distance indicating a distance between two sequential images in the image series. By limiting the amount of information that is stored at the navigation system, the storage module at the navigation system can be used more efficiently.

It will be appreciated that numerous specific details are set forth in order to provide a thorough understanding of the example embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description and the drawings are not to be considered as limiting the scope of the embodiments described herein in any way, but rather as merely describing the implementation of the various embodiments described herein. Where considered appropriate, for simplicity and clarity of illustration, reference numerals may be repeated among the figures to indicate corresponding or analogous elements or steps.

The embodiments of the systems and methods described herein may be implemented in hardware or software, or a combination of both. These embodiments may be implemented in computer programs executing on programmable computers, each computer including at least one processor, a data storage module (including volatile memory or non-volatile memory or other data storage elements or a combination thereof), and at least one communication interface. For example, a suitable programmable computer may be a server, network appliance, embedded device, computer expansion module, personal computer, laptop, or any other computing device capable of being configured to carry out the methods described herein.

In some embodiments, the communication interface may be a network communication interface. In embodiments in which elements are combined, the communication interface may be a software communication interface, such as those for inter-process communication (IPC). In still other embodiments, there may be a combination of communication interfaces implemented as hardware, software, and combination thereof.

Program code may be applied to input data to perform the functions described herein and to generate output information. The output information is applied to one or more output devices, in known fashion.

Each program may be implemented in a high level procedural or object oriented programming and/or scripting language, or both, to communicate with a computer system. However, the programs may be implemented in assembly or machine language, if desired. In any case, the language may be a compiled or interpreted language. Each such computer program may be stored on a storage media or a device (e.g. ROM, magnetic disk, optical disc) readable by a general or special purpose programmable computer, for configuring and operating the computer when the storage media or device is read by the computer to perform the procedures described herein. Embodiments of the system may also be considered to be implemented as a non-transitory computer-readable storage medium, configured with a computer program, where the storage medium so configured causes a computer to operate in a specific and predefined manner to perform the functions described herein.

Furthermore, the system, processes and methods of the described embodiments are capable of being distributed in a computer program product comprising a computer readable medium that bears computer usable instructions for one or more processors. The medium may be provided in various forms, including one or more diskettes, compact disks, tapes, chips, wireline transmissions, satellite transmissions, internet transmission or downloadings, magnetic and electronic storage media, digital and analog signals, and the like. The computer useable instructions may also be in various forms, including compiled and non-compiled code.

The methods and systems described herein are directed to navigating an image series based on a reference location. The image series may include at least one image and may generally include more than one related images. For example, an image series may include images generated from a Magnetic Resonance Imaging (MRI) examination or a Computed Tomography (CT) examination.

An image series may be associated with one or more image series from the same image study or from different image studies. An image study may include one or more related image series. For example, the various image series in an image study may be associated with a specific anatomy of an individual over different periods of time. Associated image series may include images associated with the same individual. The associated image series may include images associated with the same anatomy of that individual or another anatomy of that individual. For example, a first image series of a patient's brain may be associated with a second image series of that patient's brain taken at a later time.

The result of associating an image series with another image series is that any navigation action performed on one image series may also be applied to any other image series associated with that image series. In some embodiments, the associated image series may be coplanar with each other. Coplanar image series are image series that lie in the same plane or approximately the same plane. For example, a first image series is coplanar with a second image series if a normal vector for the first image series and a normal vector for the second image series are parallel to each other, or intersect each other within a predefined angle of tolerance. The angle of tolerance may be within a range of 0 to 180 degrees, for example. In some embodiments, the range for the angle of tolerance may be 0 to 25 degrees.

An image series may be manually or automatically associated with another image series. A manual association may be created by a user, and may also be applied to image series in the same image study or across different image studies that are associated with one individual. An automatic link is an association between image series of the same study based on various parameters. For example, an image series may be automatically associated with another image series if the two image series share a DICOM frame of reference identifier.

Reference is first made to FIG. 1, which illustrates a block diagram 100 of components interacting with a navigation system 110 over a network 150. The navigation system 110 includes a processor module 112, a storage module 114 and an interface module 116. As shown in FIG. 1, the navigation system 110 is in communication with an image server 120 and at least one computing device 130. The navigation system 110 may be a server computer or may be provided on one or more server computers. In some embodiments, the navigation system 110 may be provided on a computing device 130.

The image server 120 may include an image database 122, or may be in communication with a remote image database for retrieving and storing data at that remote image database. The image database 122 may store data associated with various image series. For each image series, the image database 122 may store all images within the image series or an image locator identifier for indicating where the images in that image series may be located. Data associated with each image in the image series may similarly be stored in the image database 122. For example, the image database 122 may store image metadata, such as DICOM attributes, for each image in the image series. The DICOM attributes may include, for example, image position and orientation attributes, pixel spacing, and frame of reference information. The image database 122 may also store data for indicating that an image series is associated with one or more other image series.

The computing device 130 may be any networked device operable to connect to the network 150 for accessing the navigation system 110. A networked device is a device capable of communicating with other devices over a network such as the network 150. A network device may couple to the network 150 through a wired or wireless connection. For ease of exposition, only one computing device 130 is illustrated in FIG. 1 but it will be understood that the navigation system 110 may be in communication with more than one computing devices 130.

Computing device 130 may include at least a processor and memory for storing instructions executable by the processor, and may be an electronic tablet device, a personal computer, workstation, server, portable computer, mobile device, personal digital assistant, laptop, smart phone, WAP phone, an interactive television, video display terminals, and portable electronic devices or any combination of these.

The network 150 may be any network(s) capable of carrying data including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g. Wi-Fi, WiMAX), SS7 signaling network, fixed line, local area network, wide area network, and others, including any combination of these.

The processor module 112 may include one or more processors. The processor module 112 may be configured to operate with each of the storage module 114 and interface module 116 for, at least, performing the methods described herein. For example, after receiving the reference location via the interface module 116, the processor module 112 may determine the target position for the image series in accordance with the methods described herein.

The interface module 116 may receive and/or transmit data via the network 150. The interface module 116 may receive an input from the computing device 130 via the network 150 and provide the received input to the processor module 112. For example, the interface module 116 may receive user inputs over a local area network connection via computing device 130, such as a handheld mobile device. The interface module 116 may also transmit any information generated by the navigation system 110 to the image server 120 and/or the computing device 130 via the network 150.

The storage module 114 may include data required for the operation of the navigation system 110. For example, the storage module 114 may include data associated with the reference location as well as any data associated with the image series for which a target position is determined. The data associated with the image series may include the initial series data and the separation distance. In comparison with the image database 122, the storage module 114 may be a local storage for facilitating the operation of the navigation system 110. If all data associated with each image series is loaded onto the navigation system 110, there is likely a substantial memory requirement on the navigation system 110 and the operation of the navigation system 110 may consequently be negatively affected. As well, accessing certain image data could be very time-consuming. For example, accessing DICOM attributes requires that DICOM image headers be accessed. As such, DICOM attributes can only be accessed after an image in an image series has been received. Accordingly, the data provided on the storage module 114 may generally be associated with operation of the processor module 112 for the methods described herein.

It will be understood that each of the modules described herein may be provided as one or more hardware components, one or more software components or a combination of both.

Figure 2:
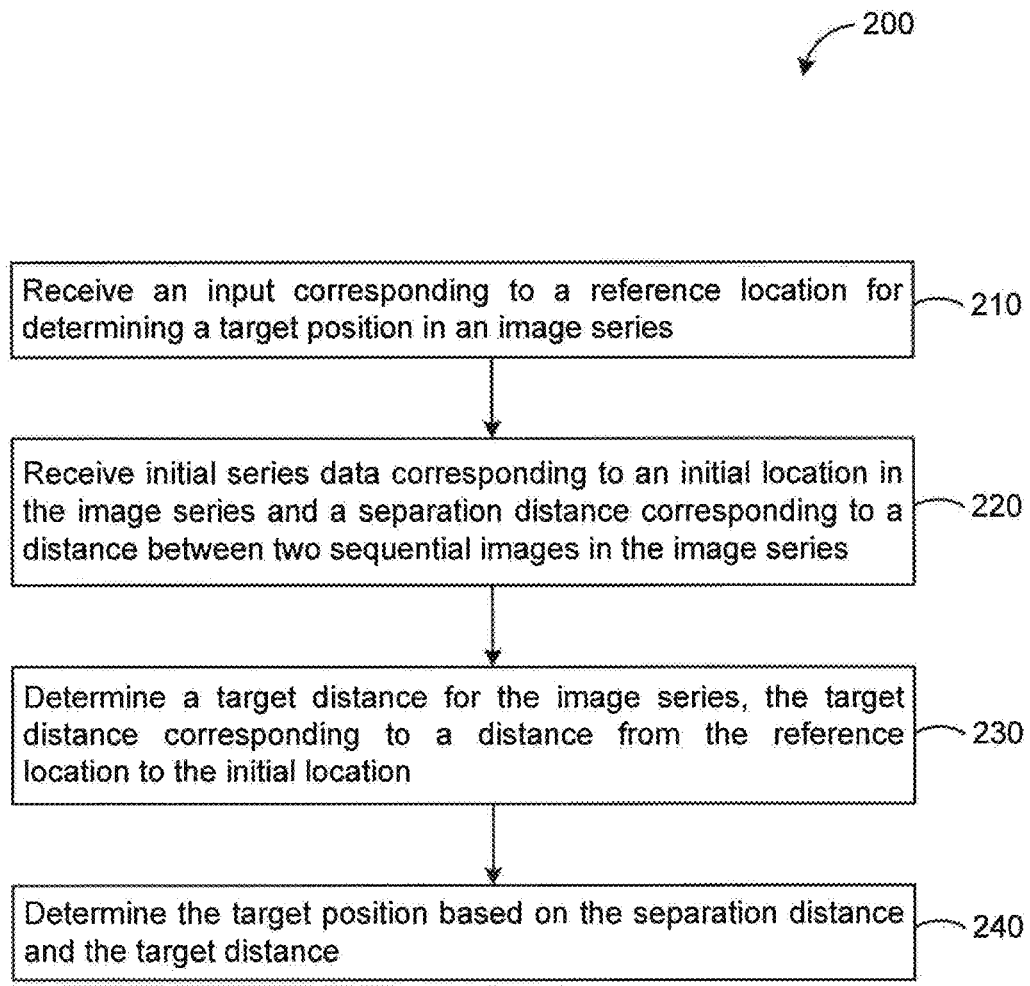
FIG. 2 is a flowchart of an example embodiment of various methods of navigating image series.

Referring now to FIG. 2, an example method of navigating an image series is shown in a flowchart diagram 200. To illustrate the method, reference will be made simultaneously to FIGS. 3, 4A and 4B, which are graphical illustrations 300, 400a and 400b, respectively, of example navigations of an image series.

At 210, the navigation system 110 receives an input corresponding to a reference location for determining a target position in an image series.

Generally, the navigation system 110 may receive input via the interface module 116. For example, an input may be provided remotely by a user at the computing device 130 and transmitted to the interface module 116 over the network 150. The input may also be provided by a user via a user interface provided by the interface module 116. The navigation system 110 may receive the input via any one or more user input devices, such as a keyboard, a pointing device, a touch screen or voice recognition system.

Figure 3:
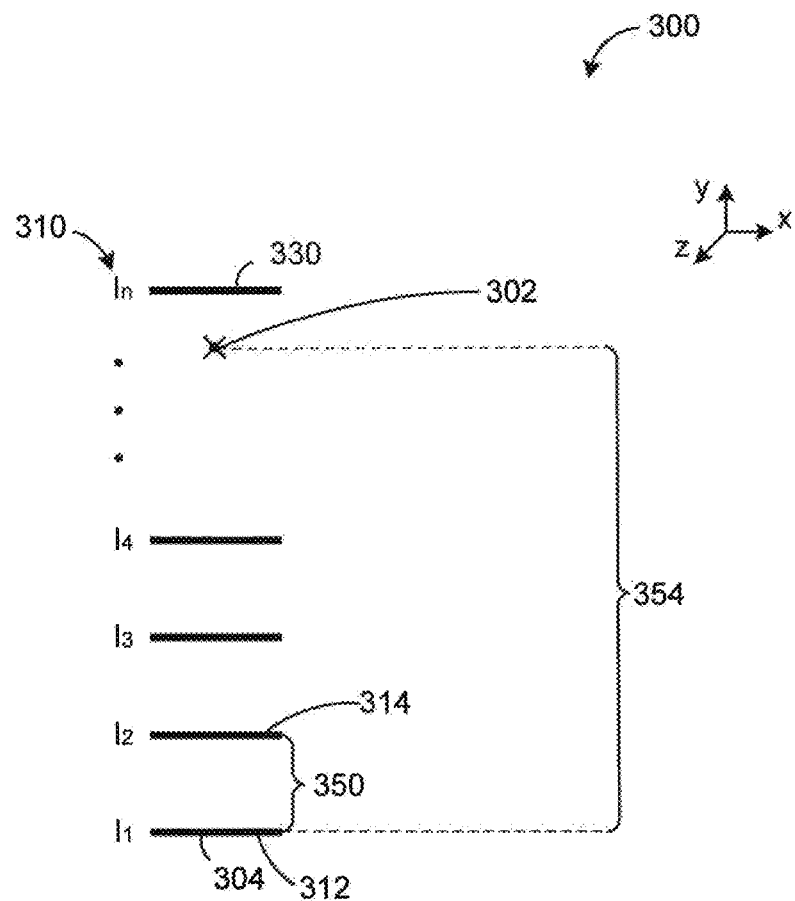
FIG. 3 illustrates navigation of an image series in accordance with an example embodiment.

Referring now to FIG. 3, an image series 310 includes an 'n' number of images. For ease of exposition, each image in the image series 310 is associated with an image index, namely $I_1$ to $I_n$, for example. The navigation system 110 receives an input that corresponds to a reference location, such as 302 in FIG. 3. In the example of FIG. 3, the reference location 302 corresponds to a location within the image series 310. The reference location 302 may be represented using any known coordinate systems, such as the Cartesian coordinate system.

Images in image series 310 may be non-collinear. Images in image series 310 are collinear if the images in that image series 310 are associated with center points that substantially lie on a line in a three-dimensional (3D) space. The images in image series 310 may be non-collinear if one or more of those images are not associated with center points that substantially lie on a same line in a 3D space.

In some embodiments, the reference location 302 may correspond to one of the images in the image series 310. The reference location 302 may therefore be represented by an image index value. In some other embodiments, the reference location 302 may be a location separate from the image series 310.

After receiving the input corresponding to the reference location 302, the processor module 112 may determine a target position for the image series 310 based on the reference location 302. The target position may correspond to a location within the image series 310 that is in closest spatial proximity to the reference location 302.

Figure 4:
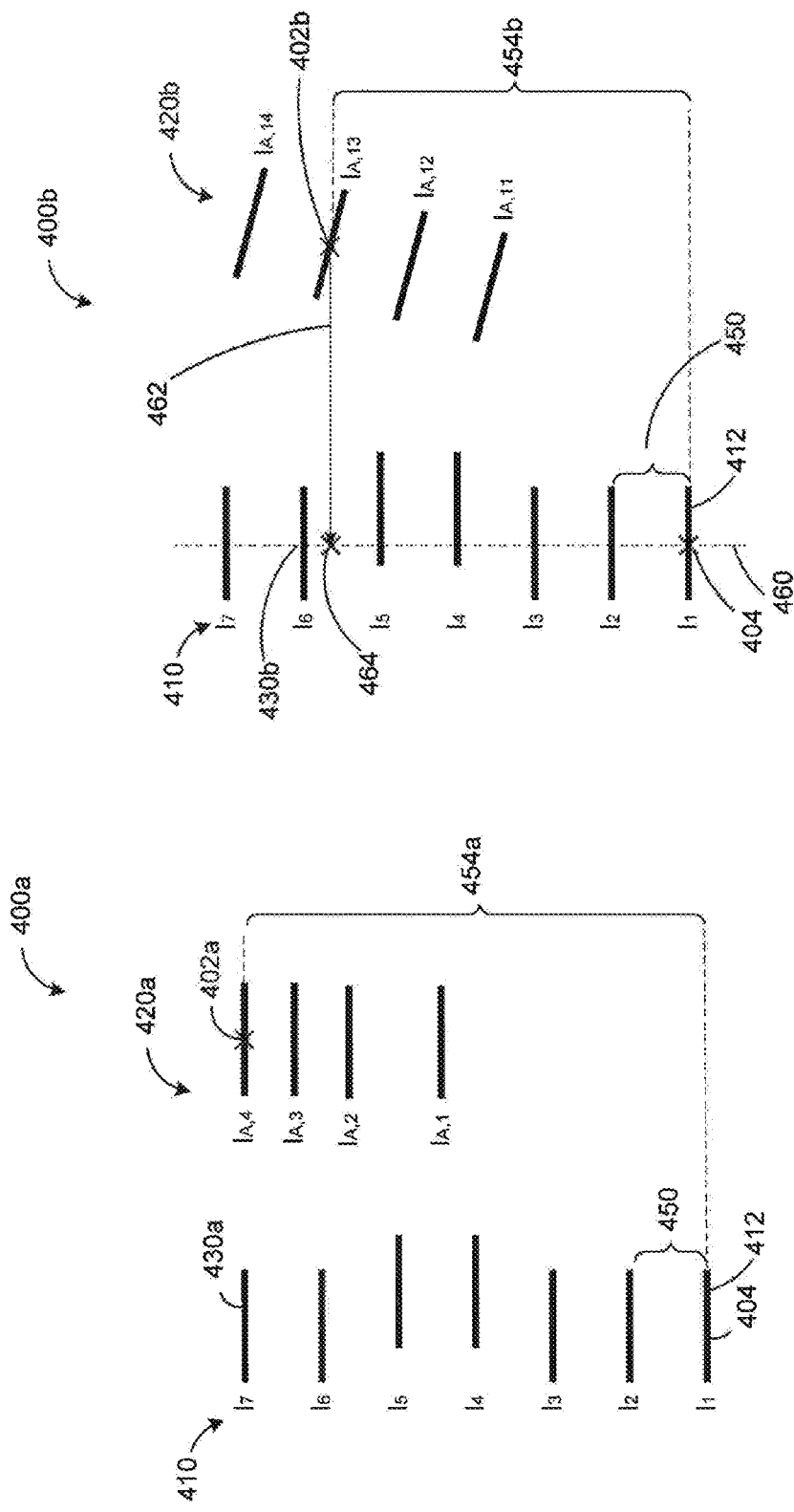
FIGS. 4A and 4B illustrate navigation of an image series in accordance with another example embodiment.

Reference is now made to FIG. 4A, which is a graphical illustration 400a of an example navigation of image series 410. In the example of FIG. 4A, image series 410 is associated with image series 420a. Image series 420a may be referred to as an active image series if the user is currently manipulating that image series or reviewing that image series. The active image series may be any image series on which the user is conducting any actions, such as rotation, navigation, zoom or mark-up. At least one of the images in the active image series may be referred to as an active image if the user is manipulating that image.

As shown in FIG. 4A, image series 410 includes seven images and each of the seven images is associated with a respective image index value from the range, $I_1$ to $I_7$. Also, images $I_1$ to $I_7$ in image series 410 are also non-collinear since center points of images $I_4$ and $I_5$ do not lie on a same line as center points of images $I_1$ to $I_3$ and images $I_6$ to $I_7$.

The image series 420a includes four images and each of those four images is also associated with a respective image index value from the range, $I_{A,1}$ to $I_{A,4}$. It will be understood that the number of images shown in FIG. 4A for each image series 410 and 420a is only for ease of exposition and that more or fewer images may be included. Unlike the example in FIG. 3, the reference location 402a of FIG. 4A corresponds to image $I_{A,4}$ in the image series 420a instead of a location in image series 410. The image $I_{A,4}$ may therefore be referred to as the active image in the active image series 420a.

At 220, the processor module 112 receives initial series data corresponding to an initial location in the image series 310 and a separation distance corresponding to a distance between two sequential images in the image series 310.

The initial series data may include data associated with at least two locations in the image series 310 or at least two images in the image series 310. For example, as illustrated in FIG. 3, the initial series data may include data associated with a first image 312, such as an image index associated with the first image 312 and any associated metadata (e.g., any relevant DICOM values, values associated with a normal vector to the first image 312 and other relevant information) and data associated with a second image 314, such as an image index value associated with the second image 314 and any associated metadata. In the example of FIG. 3, the first image 312 corresponds to an initial location 304 for the image series 310. In some embodiments, the at least two locations may be associated with sequential images, such as the first image 312 and the second image 314, in the image series 310.

A distance between the first image 312 and the second image 314 in the image series 310 may also be provided as a separation distance 350 for the image series 310. It will be understood that the separation distance 350 may represent a distance between any two sequential images in the image series 310 and not necessarily the distance between the first image 312 and the second image 314. It will be further understood that the separation distance 350 may not be uniform across the image series 310 since images in the image series 310 may be separated from each other at different distances.

After receiving the initial series data and the separation distance 350 for the image series 310, the processor module 112 may store the initial series data and the separation distance 350 in the storage module 114 in association with the image series 310. Accordingly, limited information associated with the image series 310 is stored in the storage module 114.

It will be understood that, for ease of exposition, all images in the image series 310 are illustrated in FIG. 3. However, only images associated with the initial series data are available to the processor module 112 for determining the target position.

At 230, the processor module 112 determines a target distance for the image series 310, the target distance corresponding to a distance from the reference location 302 to the initial location 304.

After receiving the initial series data and the separation distance 350 for the image series 310, the processor module 112 may determine how the reference location 302 may be related to the image series 310. As illustrated in FIG. 3, the processor module 112 may determine a target distance 354 based on how far the reference location 302 is from the initial location 304 along an axis. For example, in FIG. 3, if each of the reference location 302 and the initial location 304 is represented with Cartesian coordinates, the processor module 112 may determine the target distance 354 based on the y-axis values for each of the reference location 302 and the initial location 304. The target distance 454a in FIG. 4A may be similarly determined.

Referring now to FIG. 4B, which is a graphical illustration 400b of another example navigation of image series 410. As shown in FIG. 4B, image series 410 is associated with image series 420b. The image series 420b includes four images and each of those four images is associated with a respective image index value from the range, $I_{A,11}$ to $I_{A,14}$. For ease of exposition, image series 420b includes only four images but it will be understood that a greater or fewer number images may be included in the image series 420b.

Similar to 420a of FIG. 4A, reference location 402b of FIG. 4B corresponds to an image, namely image $I_{A,13}$, in the image series 420b. As shown in FIG. 4B, the processor module 112 may determine a target distance 454b based on a series vector 460 and an active projection 462. The processor module 112 may be configured to generate the series vector 460 based on the initial series data and to generate the active projection 462 from the reference location 402b to the series vector 460, as illustrated in FIG. 4B. A position 464 on the series vector 460 where the active projection 462 meets the series vector 460 corresponds to the reference location 402b, and may be referred to as a junction position. Accordingly, the target distance 454b corresponds to a distance along the series vector 460 that begins at the initial location 404 to the junction position 464. As described, the initial location 404 may be a position in the image series 410 or may correspond to an image in the image series 410.

Generally, the relative positions of the reference location 402b and the initial location 404 may be determined using the series vector 460 and the active projection 462. For example, as described above, the series vector 460 may include junction position 464 that corresponds to the reference location 402b. Since both the initial location 404 and the junction position 464 corresponds to a position on the series vector 460, the series vector 460 may then indirectly serve as a common axis for the reference location 402b and the initial location 404. The target distance 454b may therefore be determined based on the distance between the positions of the initial location 404 and the junction position 464 on the series vector 460.

In some embodiments, the processor module 112 may generate the series vector 460 by initializing the series vector from a substantially central portion of the initial image, such as the first image 412. The series vector 460 generally corresponds to a normal to the initial location 404. The series vector 460 may, therefore, also indicate an orientation of at least one image in the image series 410. As shown in FIG. 4B, the series vector 460 is normal to the first image 412. The processor module 112 may generate the series vector 460 based on metadata provided in the initial series data for that image series 410.

In FIG. 4B, the initial location 404 and the junction position 464 are located on the series vector 460, which is a normal to the initial location 404. As a result, the target distance 454b may be determined as the difference between the initial location 404 and junction position 464. For example, the target distance 454b may be determined based on the following formula:

$$\text{Target Distance} = (P_A \cdot N_i) - (P_i \cdot N_i)$$

where $P_A$ represents the reference location 402b, $N_i$ represents the series vector 460 as a normal unit vector and $P_i$ represents the initial location 404. As shown in the above equation, the target distance may correspond to a difference between a dot product of the reference location 402b ($P_A$) and the normal unit vector ($N_i$), and a dot product of the initial location 404 ($P_i$) and the normal unit vector ($N_i$).

The processor module 112 may, in some embodiments, initialize the active projection from the reference location 402b or at a substantially central portion of the active image, such as image $I_{A,13}$.

At 240, the processor module 112 determines the target position based on the separation distance 350 and the target distance 354.

With reference again to FIG. 3, a target position 330 is illustrated. Target position 330 corresponds to image $I_n$. As shown, the target position 330 corresponds to an image in the image series 310 that is in closest spatial proximity to the reference location 302. The target position 330 may correspond to an image or a position in the image series 310.

The processor module 112 may determine the target position under the assumption that the distances between every two sequential images in the image series 310 are uniform and are represented by the separation distance 350. However, in some embodiments, the separation distance 350 may not be uniform across the image series 310. For example, with reference again to FIG. 3, the separation distance 350 between the first image 312 and the second image 314 may not be the same as a distance between two different sequential images in the image series 310.

Reference is again made to FIG. 4A. The processor module 112 may determine a target position 430a based on the reference location 402a. The processor module 112 may, in some embodiments, determine the target position 430a by estimating a number of intermediary images located between the initial location 404 and the target position 430a. The target position 430a may therefore correspond to a target image, which is an image located away from the initial location 404 by the estimated number of intermediary images. For example, the processor module 112 may determine the number of intermediary images by dividing the target distance 454a by the separation distance 450.

In the example of FIG. 4A, the processor module 112 may determine, based on the target distance 454a and the separation distance 450, that the target image is located six images away from the initial location (image $I_1$). Accordingly, the target position 430a corresponds to image $I_7$ in the image series 410.

Similarly, in the example of FIG. 4B, the processor module 112 may determine a target position 430b based on the reference location 402b. The processor module 112 may determine, based on the target distance 454b and the separation distance 450, that the target image is located five images away from the initial location (e.g., image $I_1$). The target position 430b, therefore, may correspond to image $I_6$ in the image series 410.

Figure 5:
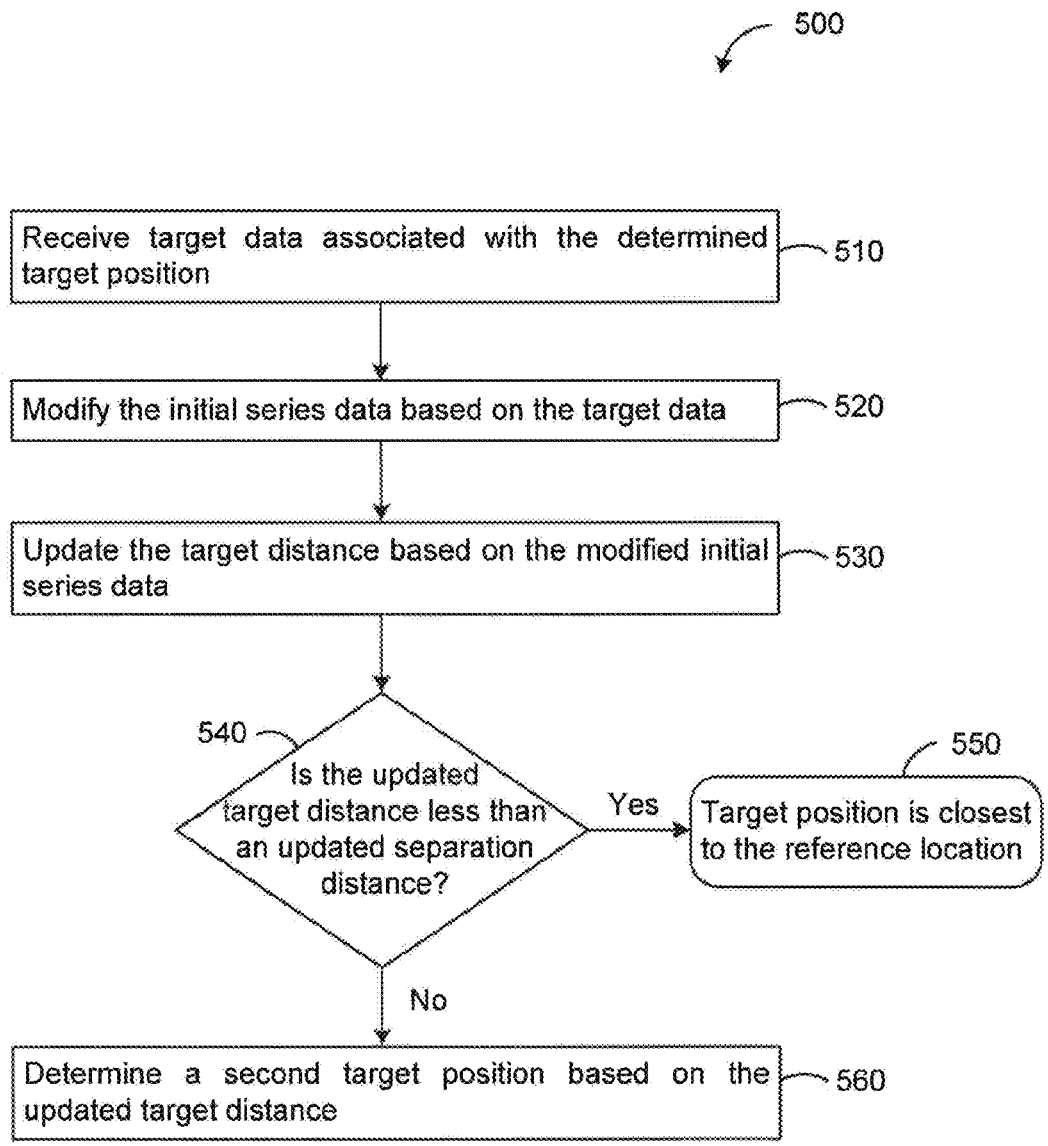
FIG. 5 is a flowchart of an example embodiment of various methods of verifying a target position.

Referring now to FIG. 5, an example method for verifying a target position (e.g., 330, 430a or 430b) determined for an image series (e.g., 310 or 410) is shown in a flowchart diagram 500. The example method in FIG. 5 may therefore be used for verifying the target position 330, 430a and 430b determined in each of FIGS. 3, 4A and 4B, respectively. To illustrate the example method shown in FIG. 5, reference will be made simultaneously to FIGS. 6A to 6C, which are graphical illustrations, 600a to 600c, respectively, of an example navigation of an image series 610.

As described, only certain information associated with the image series 610, such as a first image 612 and a separation distance 650, is available to the processor module 112 for determining a target position 630. As a result, the processor module 112 may require additional data in order to verify the target position 630.

At 510, the processor module 112 receives target data associated with the determined target position 630.

Figure 6C:
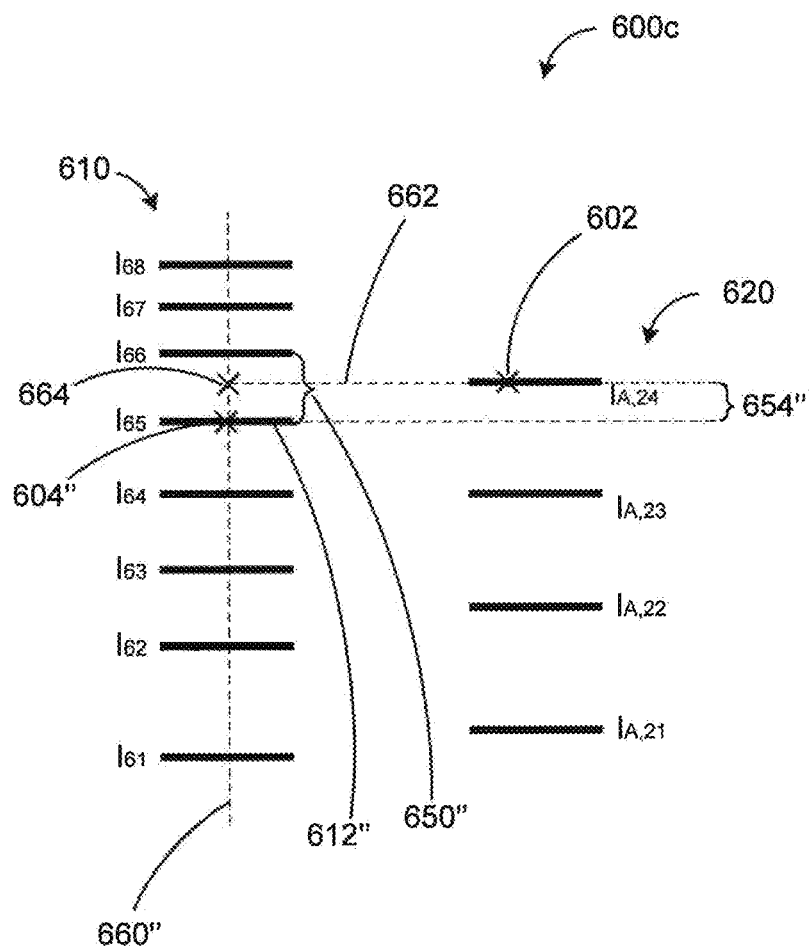

Each of FIGS. 6A to 6C illustrate an image series 610 and an image series 620. Image series 620 is associated with the image series 610. The image series 610 may be referred to as a target image series and the associated image series 620 may be referred to as the active image series. As illustrated, a reference location 602 corresponds to a position on image $I_{A,24}$ in the active image series 620. Similar to the examples in FIGS. 3, 4A and 4B, image series 610 and 620 each includes several images and those images each corresponds to an image index value. Image series 610 includes eight images and each of those eight images corresponds to an image index value from the range $I_{61}$ to $I_{68}$. Image series 620 includes four images and each of those four images corresponds to an image index value from the range $I_{A,21}$ to $I_{A,24}$. It will be understood that the image index values described herein are merely examples and that other image index values may similarly be used.

As described with reference to FIG. 2, the processor module 112 may determine the target position 630 with the use of certain information associated with the image series 610. For example, for navigating the image series 610 in FIG. 6A, the processor module 112 may determine the target position 630 using the initial series data that corresponds to an initial location 604 in the image series 610 and the separation distance 650. As illustrated in FIG. 6A, the target position 630 may correspond to a target image $I_{64}$. The target data may include data associated with the target position 630, the target image $I_{64}$ and any metadata associated with the target position 630 or the target image $I_{64}$. In some embodiments, the processor module 112 may store the received target data in the storage module 114.

At 520, the processor module 112 modifies the initial series data based on the target data.

Reference is now made to FIGS. 6A and 6B. As described with reference to 220 in FIG. 2, the initial series data may include data associated with the initial location 604, which corresponds to the first image 612. The target data may be associated with the target position 630 and therefore, also the target image $I_{64}$.

When verifying the target position 630, the processor module 112 may update the initial series data received at 220 in FIG. 2 using the target data. For example, the processor module 112 may update the initial series data to include data associated with the target image $I_{64}$. The target image $I_{64}$, therefore, may also be referred to as a second initial image 612' (see FIG. 6B, for example). A second separation distance 650' and a second initial location 604' may also be included into the initial series data. The second separation distance 650' and the second initial location 604' are associated with the second initial image 612'.

When the processor module 112 modifies the initial series data, the processor module 112 may replace existing data associated with the first image 612 with data associated with the second initial image 612'. Alternatively, the processor module 112 may add data associated with the second initial image 612' to the existing data associated with the first image 6'12.

The initial series data associated with the second initial image 612' may be different from the initial series data associated with the first image 612. For example, the values associated with the normal vector to the first image 612 may be different from the values associated with the normal vector to the second initial image 612'.

At 530, the processor module 112 updates the target distance 654 based on the modified initial series data.

As shown in FIG. 6B, the processor module 112 may determine an updated target distance 654' based on the data associated with the second initial image 612'. The processor module 112 may determine the updated target distance 654' in accordance with the example embodiments described with reference to 230 of FIG. 2. For example, the processor module 112 may determine the updated target distance 654' based on the reference location 602 and the position of the second initial image 612'.

At 540, the processor module 112 determines if the updated target distance 654 is less than half of the second separation distance 650'.

If the processor module 112 determines, at 540, that the updated target distance 654' is less than half the second separation distance 650', the target position 630 of FIG. 6A corresponds to a position in the image series 610 that is in closest spatial proximity to the reference location 602 (550 of FIG. 5). This, therefore, generally indicates that there is no other image in the image series 610 that is closer to the reference location 602 than the target position 630.

If the processor module 112 determines, at 540, that the updated target distance 654' is greater than or equal to half the second separation distance 650', the target position 630 of FIG. 6A, therefore, does not correspond to a position in the image series 610 that is in closest spatial proximity to the reference location 602. The processor module 112, therefore, may proceed to 560 of FIG. 5.

For example, as shown in FIG. 6B, the updated target distance 654' is greater than half the second separation distance 650'. This, therefore, generally indicates that there is at least another image in the image series 610 that is closer in spatial proximity to the reference location 602 than the target position 630. It may be of interest to note that, unlike image series 410, the images in image series 610 are not uniformly separated. The separation distance 650 between the first image 612 and second image 614 is different from some of the other distances between two sequential images in the image series 610, such as the distance between image $I_{62}$ and image $I_{63}$, for example.

At 560, the processor module 112 determines a second target position 630' based on the updated target distance 654'.

If the processor module 112 determines that the target position 630 is not the location in closest spatial proximity to the reference location 602, the processor module 112 may determine a second target position 630' using data associated with the second initial image 612' in accordance with the embodiments described with reference to FIG. 2. As shown in the embodiment of FIG. 6B, the second target position 630' corresponds with the image $I_{65}$. The processor module 112 may verify the second target position 630' using the embodiments described with reference to FIG. 5.

For example, as illustrated in FIG. 6C, the processor module 112 may further modify the initial series data previously modified at 520 based on target data associated with the second target position 630', or image $I_{65}$. The target image $I_{65}$, therefore, may also be referred to as a third initial image 612". The initial series data may further be modified to include a third separation distance 650" and a third initial location 604". The processor module 112 may then determine a further updated target distance 654". As shown in FIG. 6C, the further updated target distance 654" is less than half the third separation distance 650". Accordingly, the second target position 630' of FIG. 6B corresponds to a location in the image series 610 that is in closest spatial proximity to the reference location 602.

Figure 7:
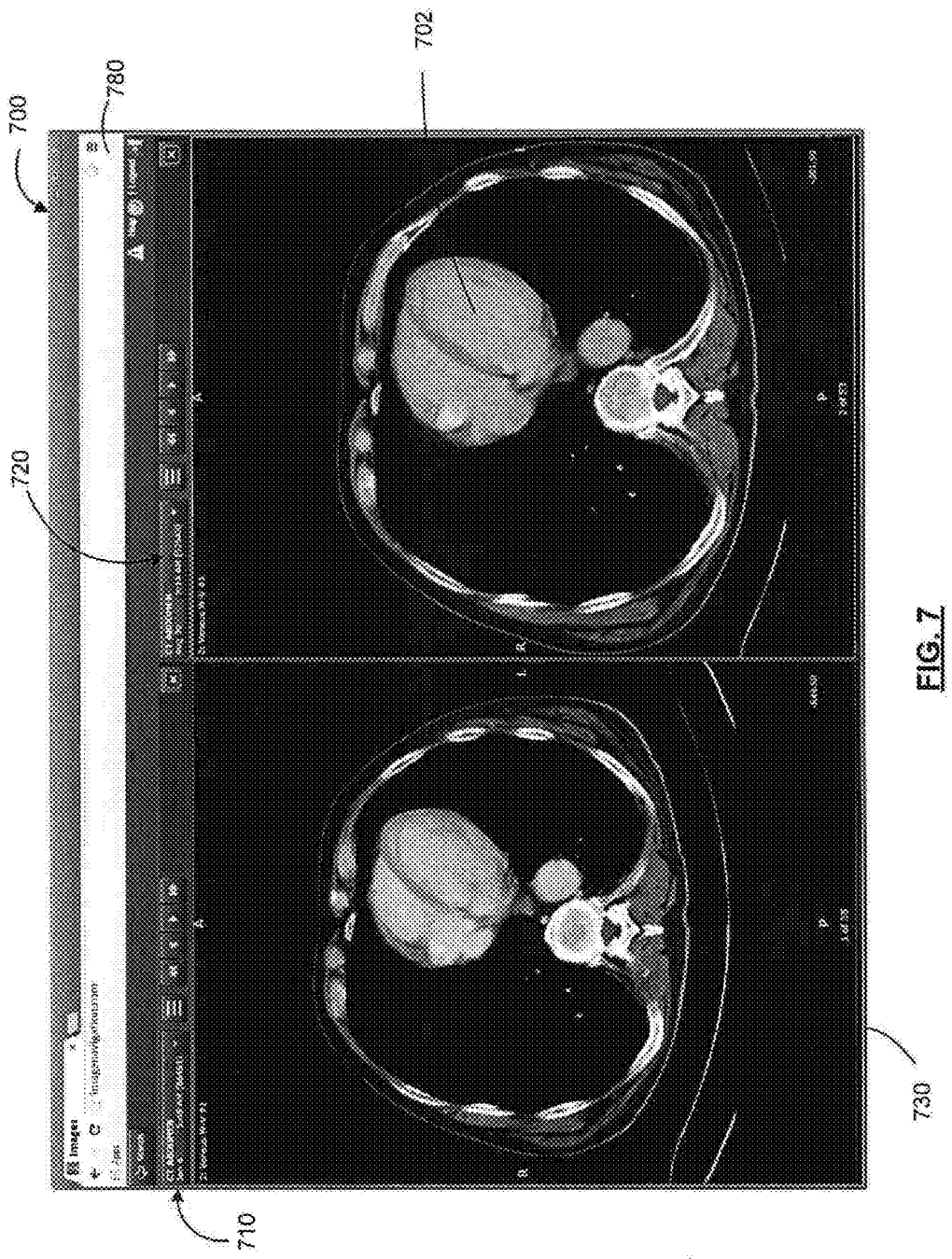
FIG. 7 is a screenshot of a user interface for navigating multiple image series in accordance with an example embodiment.

Referring now to FIG. 7, which is a screenshot 700 of an example user interface 780 for navigating multiple image series. Two image series, 710 and 720, are displayed on user interface 780. In the embodiment of FIG. 7, the image series 710 is the target image series and image series 720 is the active image series. The processor module 112 may receive an input corresponding to reference location 702 in image series 720. Based on the reference location 702, the processor module 112 may determine a target position 730 in the image series 710. After determining the target position 730, the processor module 112 may identify a corresponding target image in the image series 710 based on the target position 730. The processor module 112 may then provide the target image to the user interface 780 for display. The processor module 112 may provide the target image to the user interface 780 via the interface module 116, for example.

Figure 8A:
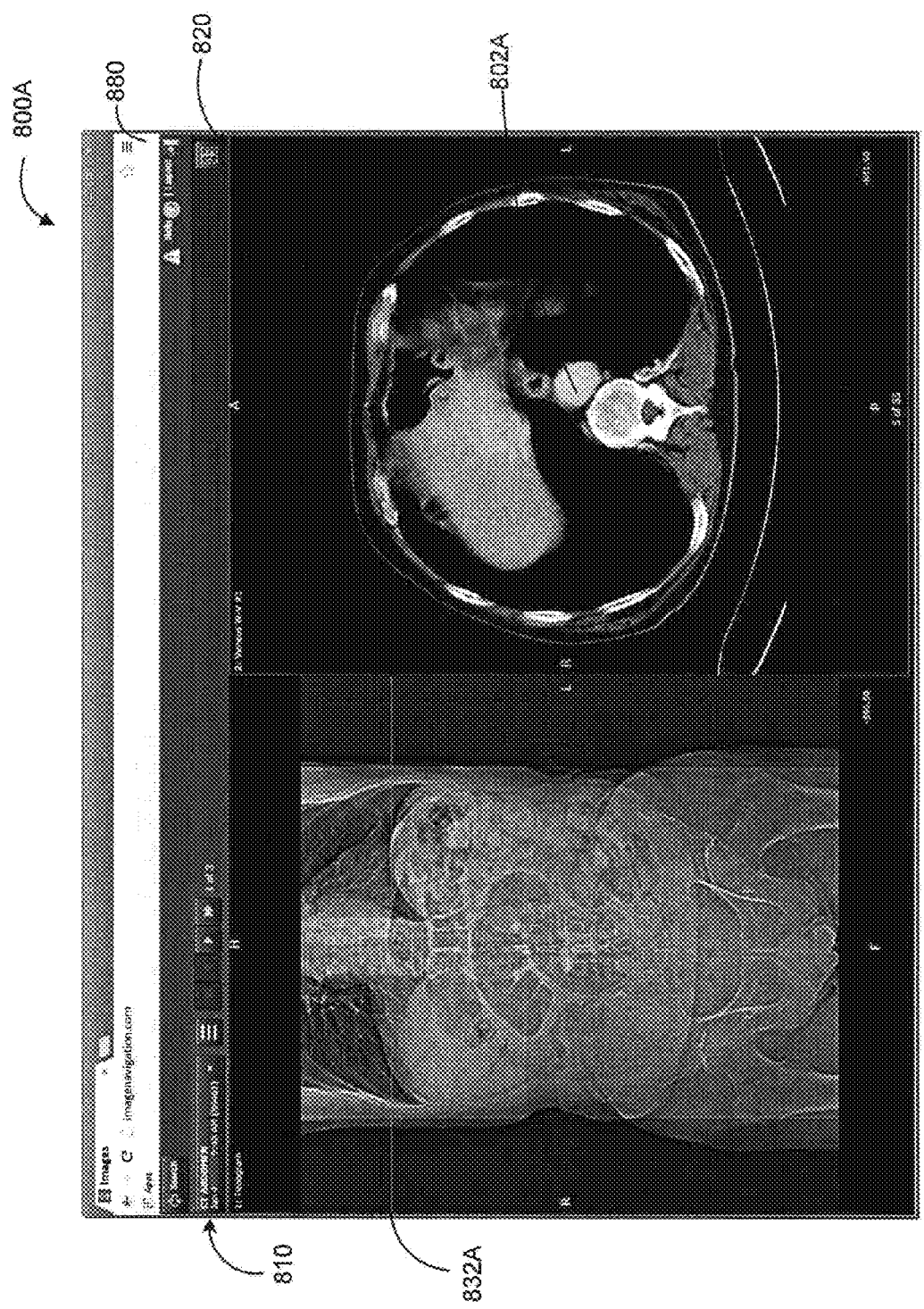
FIGS. 8A and 8B are screenshots of a user interface for navigating multiple image series in accordance with example embodiments.

With reference now to FIG. 8A, which is a screenshot 800A of another example user interface 880 for navigating multiple image series. Two image series, 810 and 820, are displayed on user interface 880. In the embodiment of FIG. 8A, the image series 810 is the target image series and image series 820 is the active image series. The processor module 112 may receive an input corresponding to reference location 802A in image series 820. Based on the reference location 802A, the processor module 112 may determine a target position in the image series 810. After determining the target position in the image series 810, the processor module 112 may display a location indicator, such as 832A, on an image for generally illustrating an area on that image that corresponds to the target position. For example, in FIG. 8, the reference location 802A is received on an image in the image series 820 displaying a cross-sectional view. The processor module 112 may then display the location indicator 832A on an image displaying a coronal view corresponding to the cross-sectional view. The location indicator 832A may generally indicate where the cross-sectional view is located on the coronal view. In some embodiments, the processor module 112 may further identify a target image in the image series 810 that corresponds to the target position and provide the target image to the user interface 880 for display.

Figure 8B:
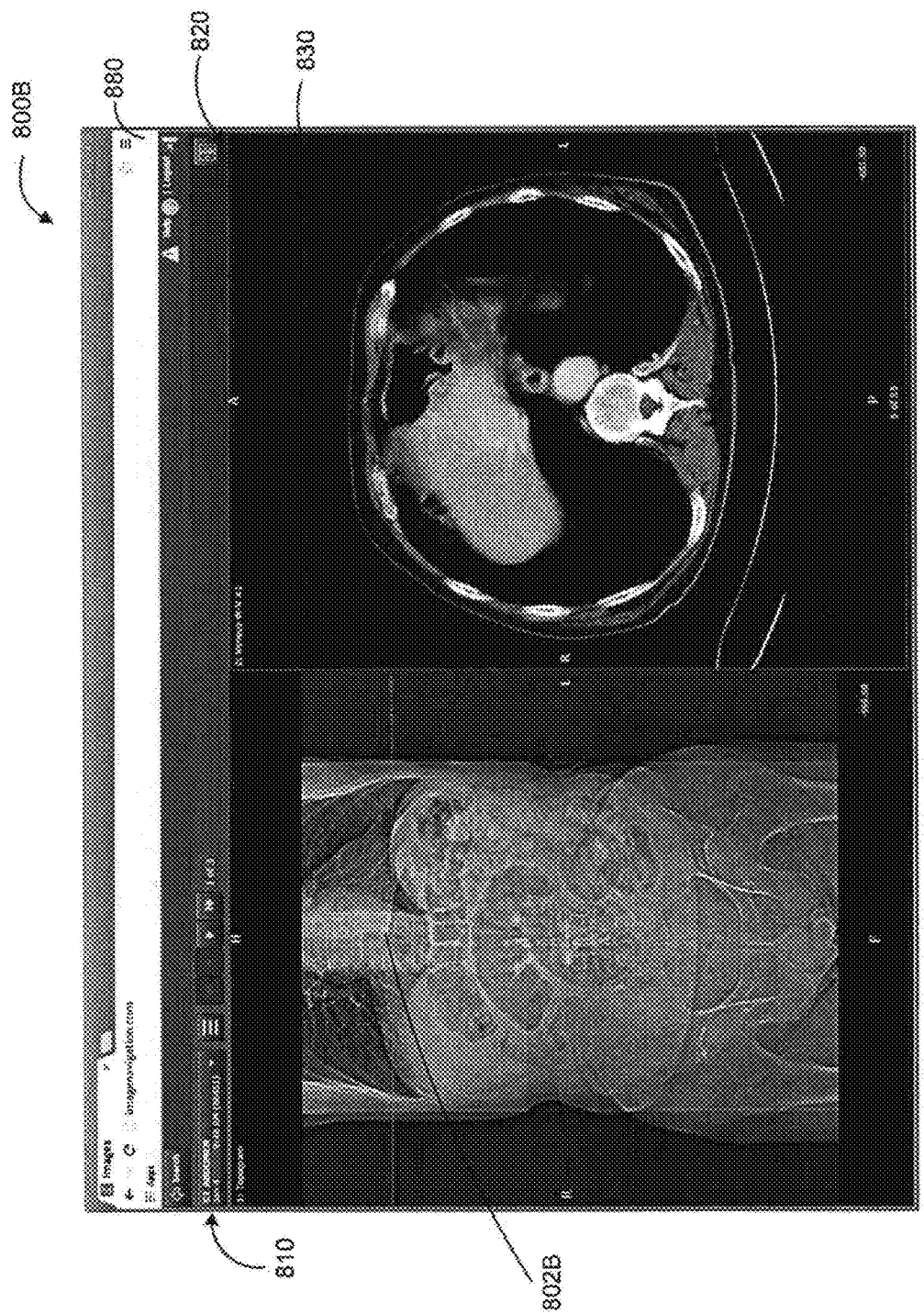

Referring now to FIG. 8B, which is a screenshot 800B illustrating another example embodiment of navigating multiple image series. In the example embodiment of FIG. 8B, image series 810 is the active image series and image series 820 is the target image series. The processor module 112 may receive an input corresponding to reference location 802B in image series 810. Based on the reference location 802B, the processor module 112 may determine a target position in the image series 820 and display a target image 830 corresponding to the target position. For example, in FIG. 8B, the reference location 802B is received on an image in the image series 810 displaying a coronal view. The processor module 112 may then display a target image 830 that is a cross-sectional view of that coronal view at the reference location 802B.

The present invention has been described here by way of example only. Various modification and variations may be made to these exemplary embodiments without departing from the spirit and scope of the invention, which is limited only by the appended claims. Also, in the various user interfaces illustrated in the figures, it will be understood that the illustrated user interface text and controls are provided as examples only and are not meant to be limiting. Other suitable user interface elements may be possible.

We claim:

1. A method for navigating an image series, the image series including at least one image, the method comprising:
receiving an input corresponding to a reference location;
operating at least one processor for determining a target position in the image series based on the reference location, the at least one processor being configured to:
receive initial series data corresponding to an initial location in the image series and a separation distance corresponding to a distance between two sequential images in the image series;
determine a target distance for the image series, wherein determining the target distance for the image series comprises:
generating a series vector for the image series based on the initial series data, the series vector being normal to the initial location; and
generating an active projection from the reference location to the series vector, the target distance corresponding to a distance between the active projection and the initial location; and
determine the target position based on the separation distance and the target distance.

2. The method of claim 1, wherein the reference location corresponds to a location within the image series.

3. The method of claim 1, wherein:
the reference location corresponds to an active image in an active image series, the active image series including at least one image and being associated with the image series; and
operating the at least one processor to determine the target position further comprises identifying a target image in the image series based on the determined target position.

4. The method of claim 3, wherein operating the at least one processor to determine the target position further comprises:
estimating a number of intermediary images located between the initial location and the target position; and
identifying the target image based on the estimated number of intermediary images, the target image being an image in the image series located from the initial location by the estimated number of intermediary images.

5. The method of claim 4, wherein estimating a number of intermediary images further comprises dividing the target distance by the separation distance.

6. A method for navigating an image series, the image series including at least one image, the method comprising:
receiving an input corresponding to a reference location;
operating at least one processor for determining a target position in the image series based on the reference location, the at least one processor being configured to:
receive initial series data corresponding to an initial location in the image series and a separation distance corresponding to a distance between two sequential images in the image series;
determine a target distance for the image series, the target distance corresponding to a distance from the reference location to the initial location; and
determine the target position based on the separation distance and the target distance, wherein determining the target position comprises:
receiving target data associated with the target position;
modifying the initial series data based on the target data;
updating the target distance and the separation distance based on the modified initial series data; and
determining if the target position corresponds to the location in the image series that is in closest spatial proximity to the reference location based on an updated target distance and an updated separation distance, wherein
the target position corresponds to the location that is in closest spatial proximity to the reference location if the updated target distance is less than half the updated separation distance and
the target image does not correspond to the location that is in closest spatial proximity to the reference location if the updated target distance is greater than half the updated separation distance.

7. The method of claim 6 further comprises:
in response to determining the target position does not correspond to the location that is in closest spatial proximity to the reference location, determining a second target position based on the updated target distance.

8. The method of claim 1, wherein:
the reference location corresponds to an active image in an active image series, the active image series including at least one image;
the image series is associated with the active image series;
the initial location corresponds to an initial image in the image series; and
generating the active projection comprises initializing the active projection at a substantially central portion of the active image.

9. The method of claim 1, wherein the initial series data further comprises data associated with at least two locations in the image series and the at least two locations corresponds to two sequential images in the image series.

10. A system for navigating an image series, the image series including at least one image, the system comprising at least one processor configured to:
receive an input corresponding to a reference location;
receive initial series data corresponding to an initial location in the image series and a separation distance corresponding to a distance between two sequential images in the image series;
determine a target distance for the image series, wherein determining the target distance for the image series comprises:
generating a series vector for the image series based on the initial series data, the series vector being normal to the initial location; and
generating an active projection from the reference location to the series vector, the target distance corresponding to a distance between the active projection and the initial location; and
determine a target position in the image series based on the separation distance and the target distance.

11. The system of claim 10, wherein the reference location corresponds to a location within the image series.

12. The system of claim 10, wherein:
the reference location corresponds to an active image in an active image series, the active image series including at least one image and being associated with the image series; and
operating the at least one processor to determine the target position further comprises identifying a target image in the image series based on the determined target position.

13. The system of claim 12, wherein operating the at least one processor to determine the target position further comprises:
estimating a number of intermediary images located between the initial location and the target position; and identifying the target image based on the estimated number of intermediary images, the target image being an image in the image series located from the initial location by the estimated number of intermediary images.

14. The system of claim 10, wherein operating the at least one processor to determine the target position further comprises:
receiving target data associated with the target position;
modifying the initial series data based on the target data;
updating the target distance and the separation distance based on the modified initial series data; and
determining if the target position corresponds to the location in the image series that is in closest spatial proximity to the reference location based on an updated target distance and an updated separation distance, wherein:
the target position corresponds to the location that is in closest spatial proximity to the reference location if the updated target distance is less than half the updated separation distance and
the target image does not correspond to the location that is in closest spatial proximity to the reference location if the updated target distance is greater than half the updated separation distance.

15. The system of claim 14, wherein verifying the target position further comprises:
in response to determining the target position does not correspond to the location that is in closest spatial proximity to the reference location, determining a second target position based on the updated target distance.

16. The system of claim 10, wherein:
the reference location corresponds to an active image in an active image series, the active image series including at least one image;
the image series is associated with the active image series;
the initial location corresponds to an initial image in the image series; and
generating the active projection comprises initializing the active projection at a substantially central portion of the active image.

17. A non-transitory computer-readable medium comprising instructions executable on at least one processor for implementing a method for navigating an image series, the image series including at least one image, the method comprising:
receiving an input corresponding to a reference location;
receiving initial series data corresponding to an initial location in the image series and a separation distance corresponding to a distance between two sequential images in the image series;
determining a target distance for the image series wherein determining the target distance for the image series comprises:
generating a series vector for the image series based on the initial series data, the series vector being normal to the initial location; and
generating an active projection from the reference location to the series vector, the target distance corresponding to a distance between the active projection and the initial location; and
determining a target position in the image series based on the separation distance and the target distance.

18. The non-transitory computer-readable medium of claim 17, wherein:
the reference location corresponds to an active image in an active image series, the active image series including at least one image and being associated with the image series; and
operating the at least one processor to determine the target position further comprises:
estimating a number of intermediary images located between the initial location and the target position; and
identifying a target image based on the estimated number of intermediary images, the target image being an image in the image series located from the initial location by the estimated number of intermediary images.

19. The non-transitory computer-readable medium of claim 17, wherein operating the at least one processor to determine the target position further comprises:
receiving target data associated with the target position;
modifying the initial series data based on the target data;
updating the target distance and the separation distance based on the modified initial series data; and
determining if the target position corresponds to the location in the image series that is in closest spatial proximity to the reference location based on an updated target distance and an updated separation distance, wherein:
the target position corresponds to the location that is in closest spatial proximity to the reference location if the updated target distance is less than half the updated separation distance and
the target image does not correspond to the location that is in closest spatial proximity to the reference location if the updated target distance is greater than half the updated separation distance.

20. The system of claim 10, wherein the initial series data further comprises data associated with at least two locations in the image series and the at least two locations corresponds to two sequential images in the image series.

21. The method of claim 1, wherein determining the target position based on the separation distance and the target distance comprises:
receiving target data associated with the target position;
modifying the initial series data based on the target data;
updating the target distance and the separation distance based on the modified initial series data; and
determining if the target position corresponds to the location in the image series that is in closest spatial proximity to the reference location based on an updated target distance and an updated separation distance, wherein:
the target position corresponds to the location that is in closest spatial proximity to the reference location if the updated target distance is less than half the updated separation distance and
the target image does not correspond to the location that is in closest spatial proximity to the reference location if the updated target distance is greater than half the updated separation distance.

* * * * *